US008617341B2

(12) United States Patent
Schneider

(10) Patent No.: US 8,617,341 B2
(45) Date of Patent: Dec. 31, 2013

(54) METHODS FOR ASSEMBLING DISPOSABLE DIAPER PANTS

(75) Inventor: Uwe Schneider, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 47 days.

(21) Appl. No.: 13/311,995

(22) Filed: Dec. 6, 2011

(65) Prior Publication Data

US 2012/0157282 A1 Jun. 21, 2012

Related U.S. Application Data

(60) Provisional application No. 61/424,750, filed on Dec. 20, 2010.

(51) Int. Cl.
*B32B 37/10* (2006.01)
*B29C 70/44* (2006.01)

(52) U.S. Cl.
USPC ............ 156/285; 156/196; 156/227; 493/405

(58) Field of Classification Search
CPC ................... A61F 13/15747; A61F 13/15585; B65H 2406/3454; B65B 63/045
USPC .......... 156/196, 216, 226, 227, 492; 493/357, 493/405
See application file for complete search history.

(56) References Cited

U.S. PATENT DOCUMENTS

| | | |
|---|---|---|
| 2,075,189 A | 3/1937 | Galligan et al. |
| 3,025,199 A | 3/1962 | Harwood |
| 3,860,003 A | 1/1975 | Buell |
| 4,107,364 A | 8/1978 | Sisson |
| 4,209,563 A | 6/1980 | Sisson |
| 4,515,595 A | 5/1985 | Kievit et al. |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |

(Continued)

FOREIGN PATENT DOCUMENTS

| | | |
|---|---|---|
| EP | 2 394 619 A1 | 12/2011 |
| JP | 07-205943 A2 | 8/1995 |
| WO | WO 2007/070113 A1 | 6/2007 |
| WO | WO 2009/032995 A1 | 3/2009 |

OTHER PUBLICATIONS

PCT International Search Report mailed Mar. 30, 2012, 11 pages.

*Primary Examiner* — Michael Orlando
*Assistant Examiner* — Marta Dulko
(74) *Attorney, Agent, or Firm* — Charles R. Matson

(57) ABSTRACT

Methods for assembling diaper pants are disclosed herein. Each diaper pant may include a chassis and two side panels extending from the chassis. The side panels join a first waist region and a second waist region of the chassis. The methods may include the step of transferring the chassis to a rotating drum including a chassis folding member, a first panel folding member and a second panel folding member. The chassis may be folded about a lateral axis by the chassis folding member. The first and second folding members may also move toward each other and radially outward relative an outer surface of the rotating drum to position second end regions of the side panels in contact with a second waist region of the chassis. The second end regions of the side panels may be connected with the second waist region.

18 Claims, 10 Drawing Sheets

(56) References Cited

U.S. PATENT DOCUMENTS

| | | | |
|---|---|---|---|
| 4,795,454 A | 1/1989 | Dragoo | |
| 4,834,735 A | 5/1989 | Alemany et al. | |
| 4,834,741 A | 5/1989 | Sabee | |
| 4,888,231 A | 12/1989 | Angstadt | |
| 4,909,803 A | 3/1990 | Aziz et al. | |
| 5,151,092 A | 9/1992 | Buell et al. | |
| 5,330,458 A | 7/1994 | Buell et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,702,551 A | 12/1997 | Huber et al. | |
| 5,779,831 A | 7/1998 | Schmitz | |
| 5,904,802 A * | 5/1999 | Niedermeyer | 156/479 |
| 5,916,661 A | 6/1999 | Benson et al. | |
| 6,107,539 A | 8/2000 | Palumbo et al. | |
| 6,545,197 B1 | 4/2003 | Muller et al. | |
| 6,620,276 B1 | 9/2003 | Kuntze et al. | |
| 6,790,798 B1 | 9/2004 | Suzuki et al. | |
| 6,811,019 B2 | 11/2004 | Christian et al. | |
| 7,013,941 B2 | 3/2006 | Schneider et al. | |
| 7,322,925 B2 | 1/2008 | Couillard et al. | |
| 7,368,027 B2 | 5/2008 | Schneider et al. | |
| 7,399,266 B2 * | 7/2008 | Aiolfi et al. | 493/424 |
| 7,521,587 B2 | 4/2009 | Busam et al. | |
| 7,587,966 B2 | 9/2009 | Nakakado et al. | |
| 2002/0111596 A1 * | 8/2002 | Fletcher et al. | 604/385.03 |
| 2004/0158212 A1 | 8/2004 | Ponomarenko et al. | |
| 2006/0212018 A1 * | 9/2006 | Roe et al. | 604/389 |
| 2007/0137011 A1 * | 6/2007 | Couillard et al. | 28/100 |
| 2009/0312730 A1 | 12/2009 | LaVon et al. | |
| 2011/0319243 A1 | 12/2011 | Fujita | |
| 2013/0029827 A1 * | 1/2013 | Fujita | 493/405 |

* cited by examiner

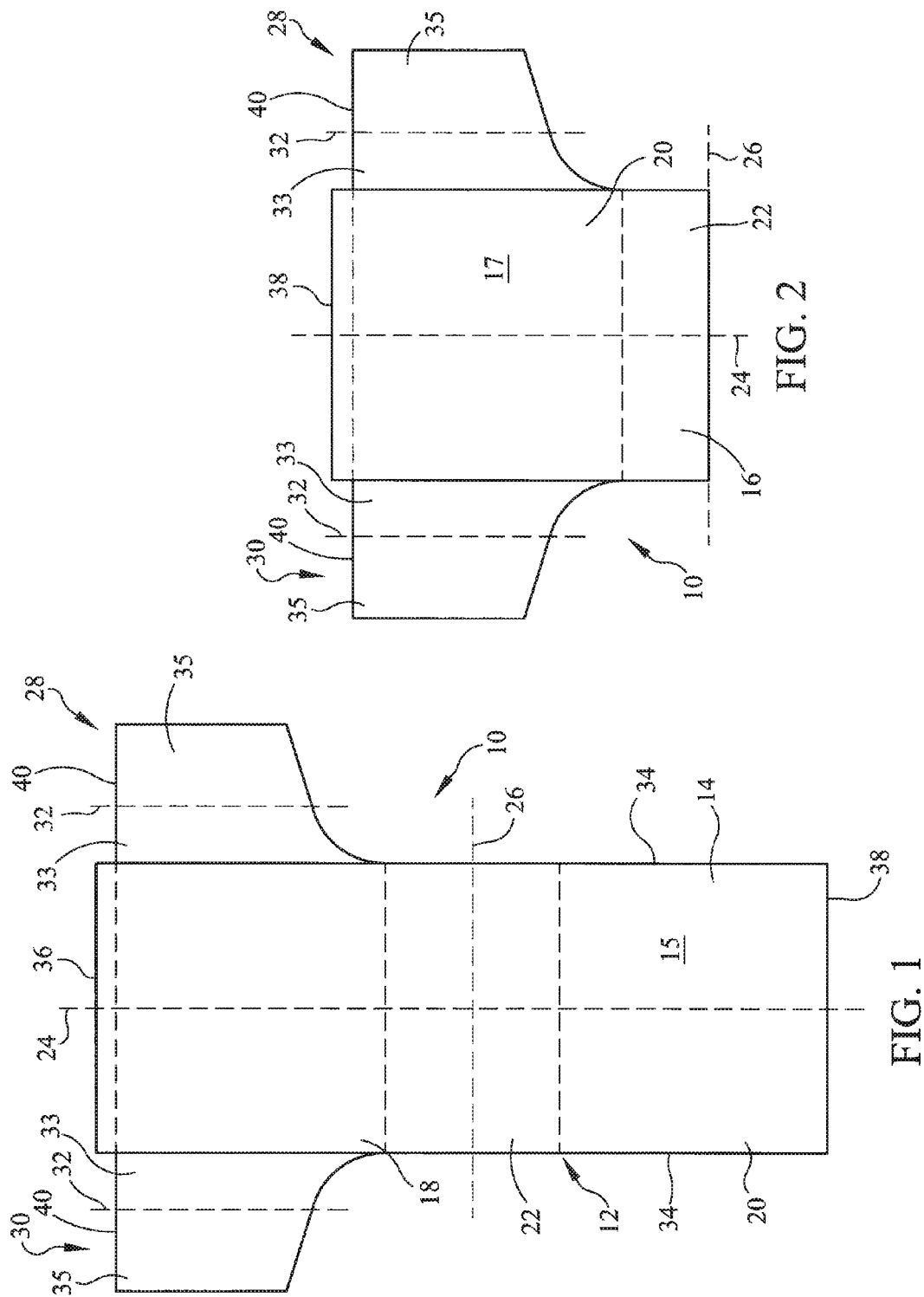

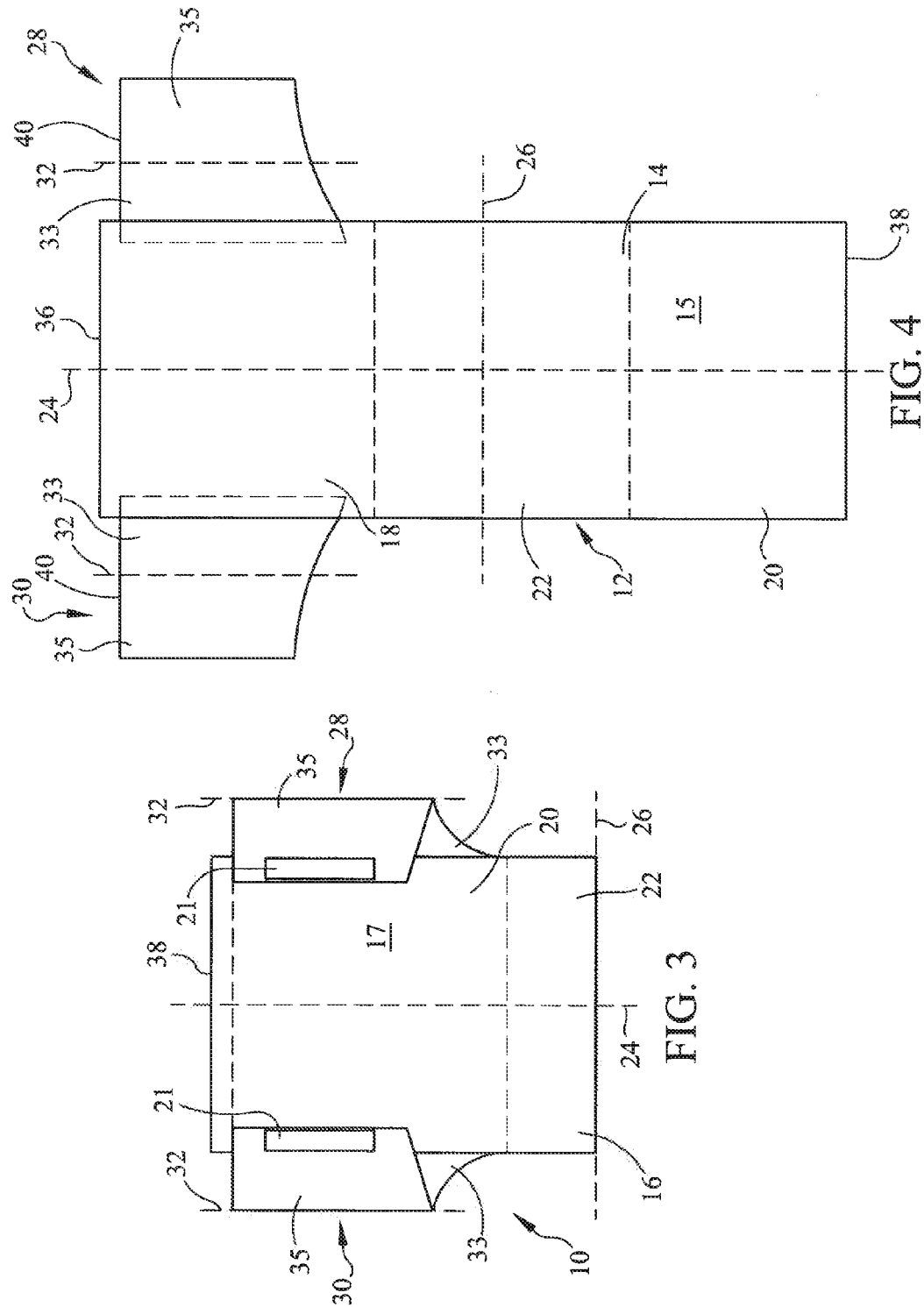

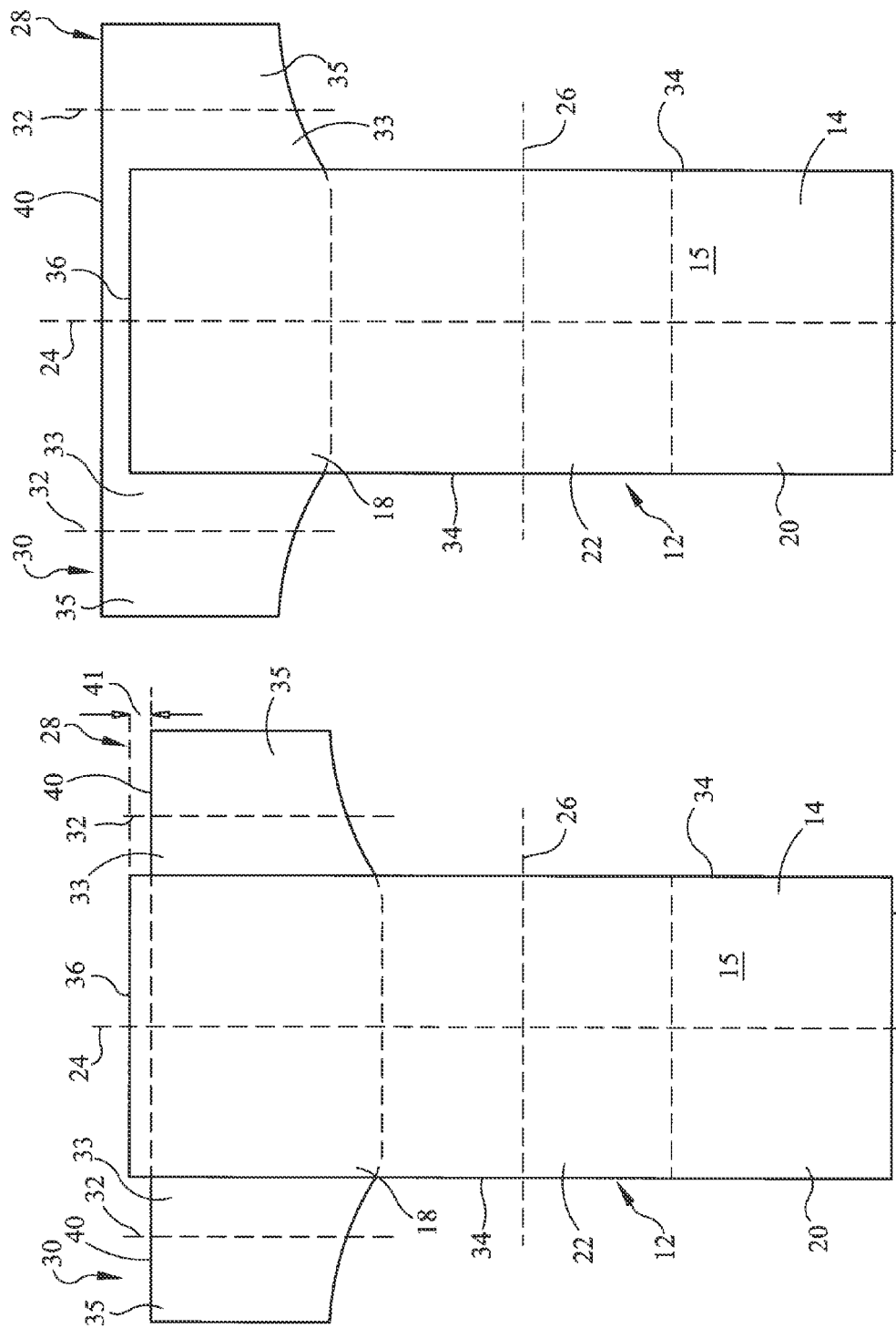

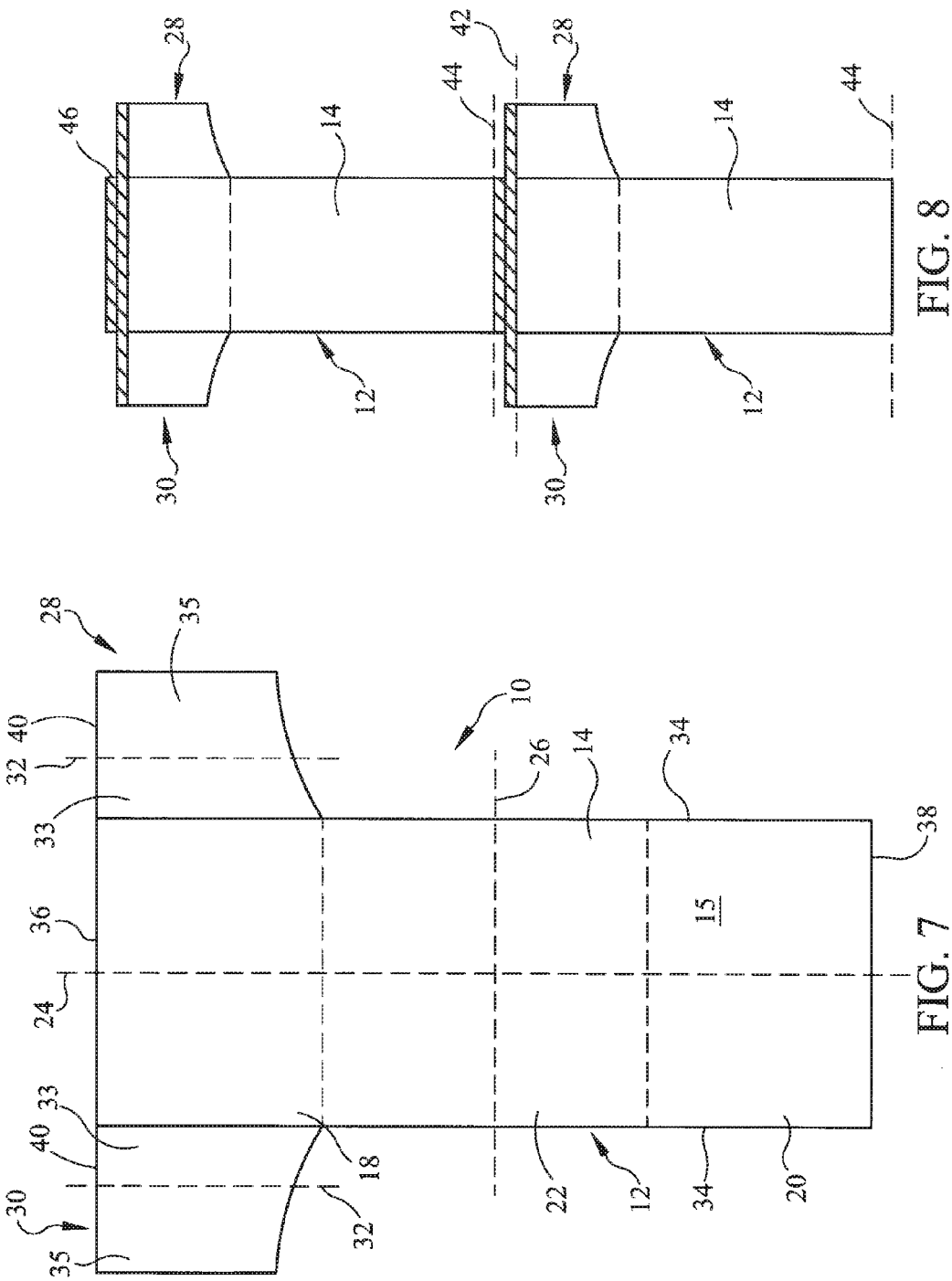

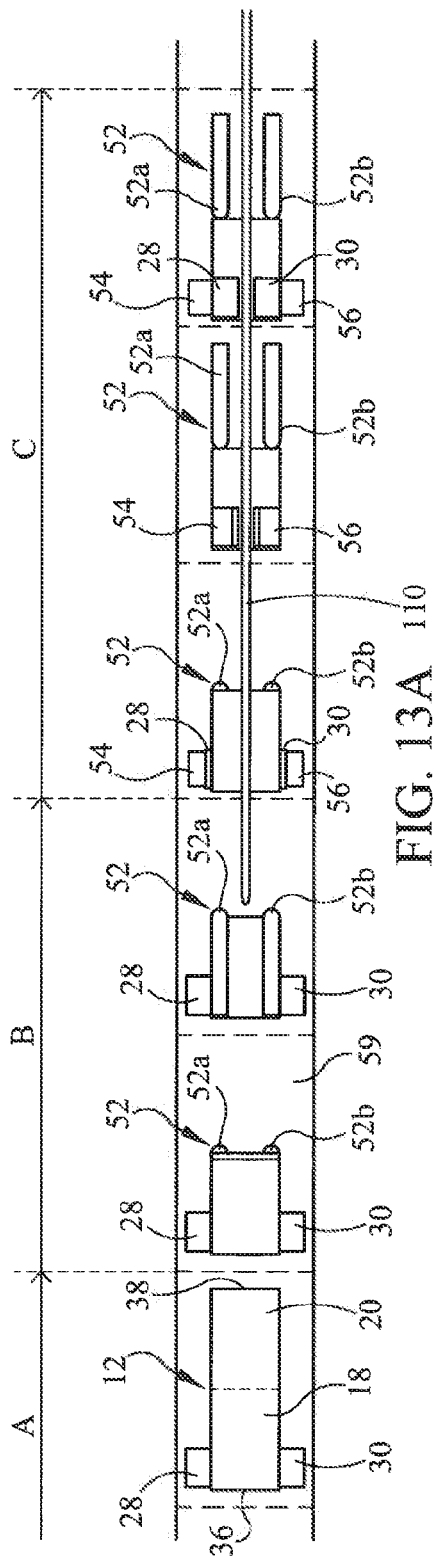
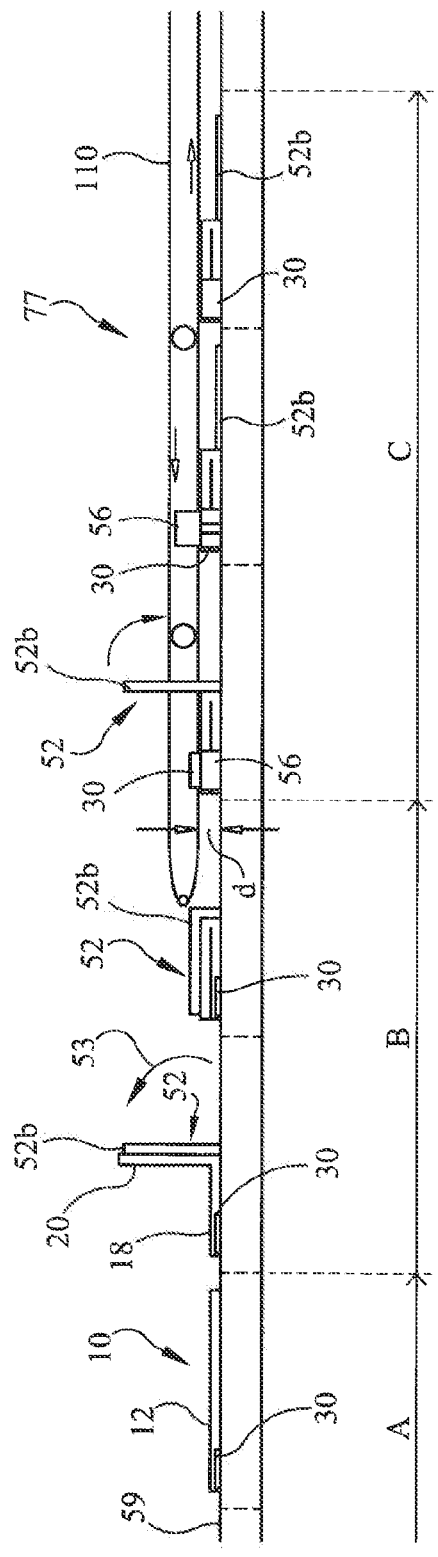

METHODS FOR ASSEMBLING DISPOSABLE DIAPER PANTS

CROSS REFERENCE TO RELATED APPLICATION

This application claims the benefit of U.S. Provisional Application No. 61/424,750, filed on Dec. 20, 2010, which is incorporated herein by reference.

FIELD OF THE INVENTION

The present disclosure generally relates to methods for assembling disposable absorbent articles, and more particularly relates to methods for assembling disposable diaper pants.

BACKGROUND OF THE INVENTION

Disposable absorbent diapers configured to be donned like pants, in that to be donned they are pulled on over a wearer's feet and up the legs rather than wrapped directly about and fastened at the wearer's lower torso like an infant diaper, have been in the market for a number of years. Such products are often marketed as "training pants" intended for children who are walking, beginning to develop independence and dress themselves, and learning to control their bodily functions so that they can transition out of diapers and into underwear. Such training pants or diaper pants provide a toilet-training child with an underwear-like garment that he or she can learn to don himself or herself in the same manner as underpants, providing a new sense of accomplishment and independence, while still providing protection against accidents. Similar articles are marketed in larger sizes and intended for older children experiencing childhood enuresis, or adults experiencing incontinence.

Currently marketed designs of diaper pants are constructed from a rectangular or hourglass-shaped precursor chassis having a liquid impermeable, garment-facing backsheet, a liquid permeable, wearer-facing topsheet, and an absorbent core between the backsheet and the topsheet. The chassis of the typical design has front and rear waist regions and a crotch region between the waist regions, and respective front and rear pairs of side panels formed of a laterally, elastically stretchable and contractible stretch laminate, extending from each of the waist regions, with the respective front and rear side panels on each side then joined together at side seams to form a pant-like structure. The side panels provide for elastic hoop-wise expansion of the article to allow it to be pulled over body contours while being donned, and elastic hoop-wise contraction to hold the article comfortably and securely in place while being worn by a wearer.

In view of the importance of disposable diaper pants, methods of manufacturing and assembling the same should be improved.

SUMMARY OF THE INVENTION

Methods for assembling diaper pants are disclosed herein. Each diaper pant may include a chassis and two side panels extending from the chassis. The side panels join a first waist region and a second waist region of the chassis. The methods may include the step of transferring the chassis to a rotating drum including a chassis folding member, a first panel folding member and a second panel folding member. The chassis may be folded about a lateral axis by the chassis folding member. The first and second folding members may also move toward each other and radially outward relative an outer surface of the rotating drum to position second end regions of the side panels in contact with a second waist region of the chassis. The second end regions of the side panels may be connected with the second waist region.

In one form, a method may be configured for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings. The method may include the steps of: connecting first end regions of the first and second side panels with the first waist region of the chassis; advancing the chassis in a machine direction on a rotating drum having an outer surface, a chassis folding member, a first panel folding member, and a second panel folding member, wherein the backsheet in the second region is positioned on the chassis folding member, and wherein the first and second side panels extend laterally outward from the first waist region with the first panel positioned on the first panel folding member and the second side panel positioned on the second panel folding member; with the chassis folding member, folding the chassis about the lateral axis to position the second waist region into a facing relationship with the first waist region; moving the first panel folding member and the second panel folding member toward each other and radially outward relative the outer surface of the rotating drum to position second end regions of the first and second side panels in contact with the second waist region of the chassis; and connecting the second end regions of the first and second side panels with the second waist region.

In another form, a method may be configured for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings. The method may include the steps of: connecting first end regions of the first and second side panels with the first waist region of the chassis; advancing the chassis in a machine direction on a rotating drum having an outer surface, a chassis folding member, a first panel folding member, and a second panel folding member, wherein the backsheet in the second region is positioned on the chassis folding member, and wherein the first and second side panels extend laterally outward from the first waist region with the first panel positioned on the first panel folding member and the second side panel positioned on the second panel folding member; pivoting each of the first panel folding member and the second panel folding member about a respective virtual axis toward each other and radially outward relative the outer surface of the rotating drum to position second end regions of the first and second side panels in contact with the second waist region of the chassis; with the chassis folding member, folding the chassis about the lateral axis to position the second waist region into a facing relationship with the first waist region; and connecting the second end regions of the first and second side panels with the second waist region.

BRIEF DESCRIPTION OF THE DRAWINGS

FIG. 1 is a top view of a diaper pant in an unfolded configuration in accordance with one non-limiting embodiment of the present disclosure.

FIG. 2 is a top view of the diaper pant of FIG. 1 in a folded configuration, but with first and second side panels in an unfolded configuration in accordance with one non-limiting embodiment of the present disclosure.

FIG. 3 is a top view of the diaper pant of FIG. 1 in a folded configuration and with the first and second side panels in a folded configuration in accordance with one non-limiting embodiment of the present disclosure.

FIG. 4 is a top view of another diaper pant in an unfolded configuration in accordance with one non-limiting embodiment of the present disclosure.

FIG. 5 is a top view of yet another diaper pant in an unfolded configuration in accordance with one non-limiting embodiment of the present disclosure.

FIG. 6 is a top view of still another diaper pant in an unfolded configuration in accordance with one non-limiting embodiment of the present disclosure.

FIG. 7 is a top view of still another diaper pant in an unfolded configuration in accordance with one non-limiting embodiment of the present disclosure.

FIG. 8 is a top view of two diaper pants in an unfolded configuration before separation in accordance with one non-limiting embodiment of the present disclosure.

FIG. 13A is a linear top view of the surface of the rotating drum in accordance with one non-limiting embodiment of the present disclosure.

FIG. 13B is an elevational side linear view of the rotating drum corresponding to FIG. 13A.

DETAILED DESCRIPTION OF THE INVENTION

Figure 9:
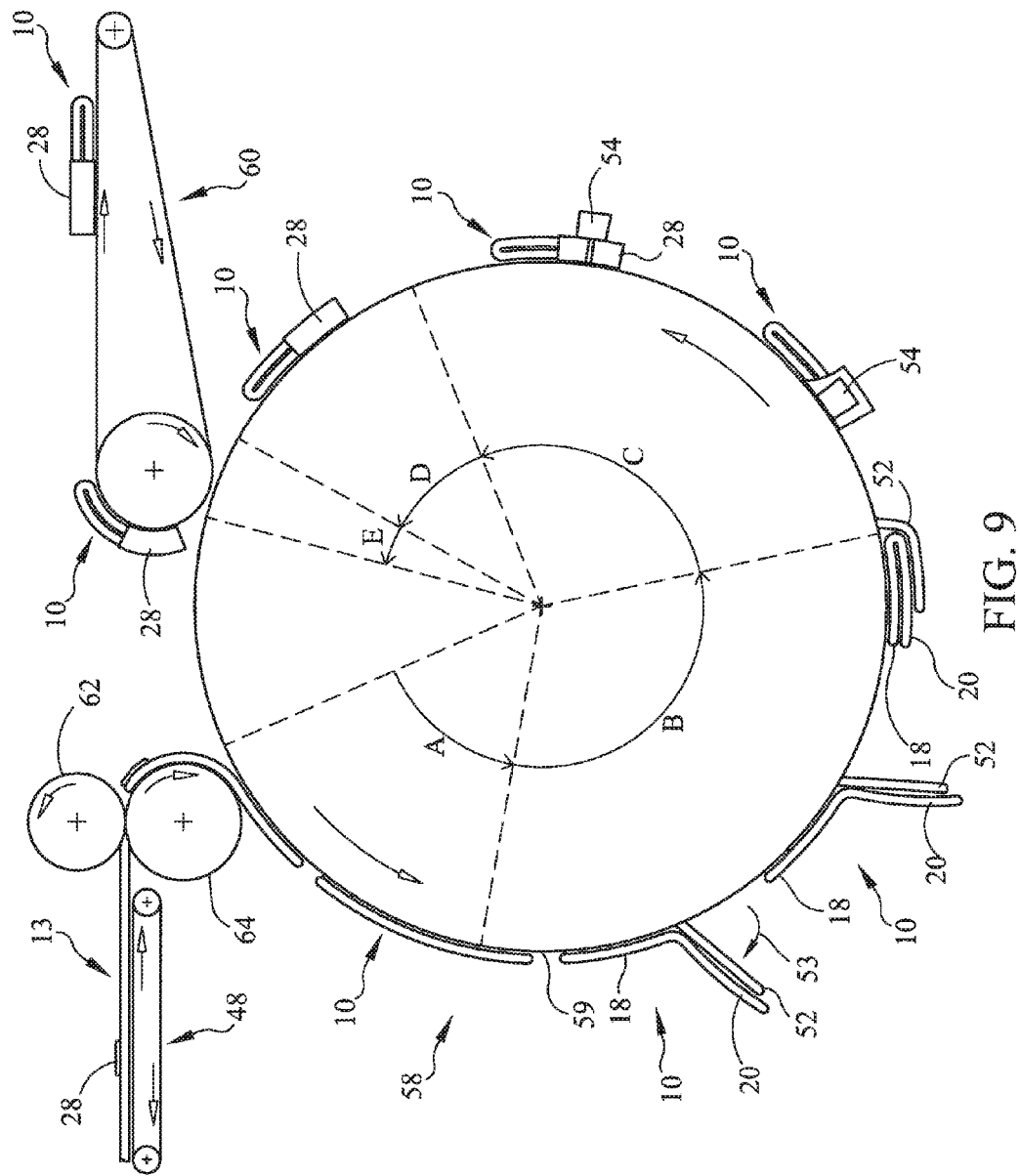
FIG. 9 is a schematic illustration of a diaper pant being assembled in accordance with one non-limiting embodiment of the present disclosure.

The following term explanations may be useful in understanding the present disclosure:

The term "absorbent article" is used herein to refer to consumer products whose primary function is to absorb and retain soils and wastes. Non-limiting examples of absorbent articles include diapers, training pants, pull-on pant-type diapers, refastenable diapers or pant-type diapers, incontinence briefs and undergarments, diaper holders and liners, feminine hygiene garments such as panty liners, absorbent inserts, and the like.

The term "bi-fold" means the leading edge portion and the trailing edge portion of an article on a production line are brought together in a face-to-face configuration once the article is folded about a fold line extending laterally across the article as the article moves in the machine direction of travel.

The term "cross direction" (CD) is used herein to refer to a direction that is generally perpendicular to the machine direction.

The term "diaper" is used herein to refer to an absorbent article generally worn by infants, children, and incontinent persons about the lower torso.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant, child, or adult wearers. A pant can be configured with a continuous or closed waist opening and at least one continuous, closed, leg opening as packaged, prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed or combinations thereof).

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "joined" encompasses configurations whereby an element is directly secured to another element by affixing the element directly to the other element, and configurations whereby an element is indirectly secured to another element by affixing the element to intermediate member(s) which in turn are affixed to the other element.

The term "lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal."

The term "machine direction" (MD) is used herein to refer to the direction of material flow through a process. In addition, relative placement and movement of material can be described as flowing in the machine direction through a process from upstream in the process to downstream in the process.

Current disposable diaper pants present at least several challenges. Because the diaper pants are "disposable" and the industry is highly competitive (factors that exert downward pressure on pricing), the business of manufacturing disposable diaper pants requires large scale and production volume for success. Thus, in addition to product quality, performance, fit, appearance, and consumer satisfaction, cost and material conservation may be an ever-present and ever-important objective. Elastomeric materials used as components of side panels may be among the more expensive components of many current disposable diaper pant designs. Consequently, inclusion of such materials to any extent that is unnecessary to provide intended functions (e.g. elastic stretch and contraction) may be undesirable.

The amount of overall lateral hoop-wise expansion available in a disposable diaper pant is affected by the lateral width of the side panels (i.e., the greater the lateral width of the side panel, the greater the amount of lateral expansion that it will provide). Thus, the respective front and rear side panels must be of a sufficient lateral width to provide for the amount of lateral hoop stretch required for the intended wearer to easily and comfortably don the diaper pant. Generally, increasing stretch capability by increasing the lateral width of the side panels provides for easier and more comfortable donning. On the other hand, once the diaper pant is donned and in wearing position on the wearer, contraction is required to provide a secure, neat fit and exudate containment functionality. If the side panels are excessively wide, the side panels may not be stretched enough in the wearing position to provide sufficient contractive securing tension, and an unacceptably loose/sloppy fit may result. Generally, decreasing the lateral width of the side panels may increase the snugness, neatness, and security of the fit and containment functionality. Thus, in designing side panels and selecting their width, competing and conflicting objectives are presented.

Further, the precursor front and rear side panels must have additional lateral width available to form the seams along which they are to be attached. The seams typically include a section of the side panels that is relatively fixed, such that it cannot serve to provide stretch capability. Thus, in one sense, the stretch capability of the portions of the side panel material (including the relatively expensive elastomeric materials) required for side seams is wasted. Considering the production volumes required for competitiveness in the market, this is not an insignificant factor.

Additionally, the typical chassis, and especially the liquid impermeable backsheet thereof, will be required to be of a certain lateral width at the front and rear waist regions in order to provide desired containment of urine or other liquid exudates, and a desired width of the envelope structure containing the absorbent core. The needed lateral width of the backsheet will take up substantial portions of the lateral waist circumference. This leaves only a smaller fraction of the overall waist band length (at the side-hip areas) available for side panels. In order to provide the stretch capability needed to strike the balance between the need for ease of donning and a secure fit, relatively high-performance elastomeric material is needed for the side panels—which is relatively expensive. Some designs have added elastically stretchable members and suitable accompanying construction to the rear and/or front waist regions to supplement waistband stretch capability. This approach, however, adds its own cost and complexity to the design.

Further, it is often desirable for a diaper pant to be quickly and easily removable (such as when soiled with exudates), without the necessity of having to pull the pant down over the wearer's legs and feet. For this reason, it may be desirable that portions of the pant are easily separable by the caregiver or wearer at one or more defined locations, so that it can be conveniently and neatly removed. One currently available design addresses this need by providing side seams held together only by strips of hook-type fastener components engaged with a compatible receiving material, which will allow relatively easy separation along the side seam when the caregiver or wearer applies requisite separating forces across the seam. However, this approach does not help with materials savings and in some circumstances may add cost and complexity to the design. Other design approaches have employed side seams in which the respective front and rear stretch panels are permanently bonded together. Although such approaches decrease the possibility of unintended separation, they also reduce the ease of removal.

In view of the foregoing, the design needs, and costs of materials typically used to make disposable diaper pants, a need exists for improvements that will conserve materials and improve lateral hoop-wise stretch performance and wearer/caregiver convenience. Furthermore, methods of manufacturing and assembling these disposable diaper pants are also needed.

FIGS. 1-3 show an embodiment of a disposable diaper pant 10. The diaper pant 10 may comprise a chassis 12 comprising a topsheet 14 forming at least a portion of a wearer-facing surface 15, a backsheet 16 forming at least a portion of a garment-facing surface 17, and an absorbent core (not illustrated) disposed between the top sheet 14 and the backsheet 16. The chassis 12 may comprise a first waist region 18 longitudinally opposed to a second waist region 20 and a crotch region 22 located between the first and second waist regions 18 and 20. Each chassis 12 may have a longitudinal axis 24 and a lateral axis 26. In some embodiments, a first side panel 28 and a second side panel 30 may extend laterally outward from the first waist region 18 or, in other embodiments, the first side panel 28 and the second side panel 30 may extend laterally outward from the second waist region 20. The first side panel 28 and the second side panel 30 may join the first waist region 18 and the second waist region 20 to form a waist opening and a pair of leg openings in the diaper pant 10. The first side panel 28 and the second side panel 30 may each have a fold line 32 about which a second end region of a side panel may be folded laterally inward over a first end region of the side panel. In some embodiments, the fold lines 32 are not structurally incorporated into the first side panel 28 and the second side panel 30. Instead, the first side panel 28 and the second side panel 30 may be generally homogenous in structure and not prone to, or otherwise configured to, fold along any particular line.

In some embodiments, the topsheet 14 may comprise at least a portion of the wearer-facing surface 15, which is configured to be positioned against a portion of a wearer's body when the diaper pant 10 is donned. The topsheet 14 may be compliant, soft feeling, and non-irritating to the wearer's skin and may be elastically stretchable in one or more directions. Further, the topsheet 14 may be liquid pervious, permitting liquids (e.g., menses, urine, and/or runny feces) to penetrate through its thickness. Various topsheets may also comprise a hydrophilic material, for example, which is configured to draw bodily fluids into an absorbent core of the chassis 12 when these fluids are expelled from the body. A suitable topsheet 14 may be manufactured from a wide range of materials, such as woven and nonwoven materials, apertured or hydroformed thermoplastic films, apertured nonwovens, porous foams, reticulated foams, reticulated thermoplastic films, and/or thermoplastic scrims, for example. Suitable apertured films may comprise those described in U.S. Pat. Nos. 5,628,097, 5,916,661, 6,545,197, and 6,107,539, which are all incorporated by reference herein in their entireties. Apertured film topsheets typically may be pervious to bodily exudates, yet non-absorbent, and have a reduced tendency to allow fluids to pass back through and rewet the wearer's skin. Suitable woven and nonwoven materials may comprise natural fibers, such as, for example, wood or cotton fibers, synthetic fibers, such as, for example, polyester, polypropylene, or polyethylene fibers, or combinations thereof. If the topsheet 14 comprises fibers, the fibers may be spunbond, carded, wet-laid, meltblown, hydroentangled, or otherwise processed, for example, as is generally known in the art.

In some embodiments, the backsheet 16 may comprise at least a portion of the garment-facing surface 17, which is configured to be positioned against garments or undergarments when the diaper pant 10 is donned. The backsheet 16 may be impervious, or at least partially impervious, to fluids or body exudates (e.g., menses, urine, and/or runny feces) and may be manufactured from a thin plastic film, although other flexible liquid impervious materials may also be used. The backsheet 16 may prevent the body exudates or fluids absorbed and contained in an absorbent core of the diaper pant 10 from wetting articles which contact the diaper pant 10, such as bedsheets, pajamas, clothes, and/or undergarments, for example. The backsheet 16 may comprise a woven or nonwoven material, polymeric films, such as thermoplastic films of polyethylene or polypropylene, and/or a multi-layer or composite materials comprising a film and a nonwoven material (e.g., having an inner film layer and an outer nonwoven layer). In some embodiments, a suitable backsheet may comprise a polyethylene film having a thickness of from about 0.012 mm (0.5 mils) to about 0.051 mm (2.0 mils), for example. Examples of polyethylene films are manufactured by Clopay Corporation of Cincinnati, Ohio, under the designation BR-120 and BR-121, and by Tredegar Film Products of Terre Haute, Ind., under the designation XP-39385. In various embodiments, the backsheet 16 may be embossed and/or matte-finished to provide a more cloth-like appearance. Furthermore, the backsheet 16 may permit vapors to escape from the absorbent core of the diaper pant 10 (i.e., the backsheet 16 is breathable), while still preventing, or at least inhibiting, fluids or body exudates from passing through the backsheet 16. In some embodiments, the size of the backsheet 16 may be dictated by the size of the diaper pant 10 and the design or configuration of the diaper pant 10 to be formed, for example.

In some embodiments, the absorbent core may be disposed between the topsheet 14 and the backsheet 16. In various embodiments, more than one absorbent core or more than one absorbent core layer may be provided in a single diaper pant, for example. The absorbent core(s) may be any suitable size or shape that is/are compatible with the diaper pant 10. Example absorbent structures for use as the absorbent core of the present disclosure that have achieved acceptance and commercial success are described in U.S. Pat. Nos. 4,610, 678, 4,673,402, 4,888,231, and 4,834,735, which are all incorporated by reference herein in their entireties.

In some embodiments, suitable absorbent cores may comprise cellulosic airfelt material. For instance, such absorbent cores may comprise less than about 40%, 30%, 20%, 10%, 5%, or even 1% of the cellulosic airfelt material as determined by weight. Additionally, such an absorbent core may be primarily comprised of an absorbent gelling material in amounts of at least about 60%, 70%, 80%, 85%, 90%, 95%, or even about 100%, as determined by weight. Furthermore, a portion of the absorbent core may comprise a microfiber glue (if applicable). Such absorbent cores, microfiber glues, and absorbent gelling materials are described in U.S. Pat. Nos. 5,599,335, 5,562,646, 5,669,894, 6,790,798, and 7,521,587 and in U.S. Patent Publication No. 2004/0158212, which are all incorporated by reference herein in their entireties.

In some embodiments, although not illustrated, the chassis 12 of the diaper pant 10 may comprise longitudinally extending and laterally opposing leg cuffs that are disposed on the wearer-facing surface 15 of the chassis 12. The leg cuffs may comprise one or more elastic gathering members disposed at or adjacent a proximal edge thereof. In addition to the elastic gathering members, one or more of the leg cuffs may comprise one or more elastic strands disposed at or adjacent a distal edge thereof. The elasticized leg cuffs may comprise several embodiments for reducing the leakage of body exudates or fluids in the leg regions. The elasticized leg cuffs are sometimes referred to as leg bands, barrier cuffs, elastic cuffs, or gasketing cuffs, for example. Suitable elasticized leg cuffs may comprise those described in U.S. Pat. Nos. 3,860,003, 4,909,803, 4,695,278, 4,795,454, 4,704,115, and 4,909,803, and U.S. Patent Publication No. 2009/0312730, which are all incorporated by reference herein in their entireties. In some embodiments, the leg cuffs may be formed by folding portions of the chassis 12 laterally inward, i.e., toward the longitudinal axis 24, to form both the respective leg cuffs and the side edges 34 of the chassis 12. In other embodiments, the leg cuffs may be formed by attaching an additional layer or layers to the chassis 12 at or adjacent to each of the respective side edges 34 of the chassis 12. In some embodiments, the chassis 12 may also comprise other elastics disposed adjacent the side edges 34, which may cause the pant 10 to form into a "U" shape when allowed to relax, thereby pulling the wearer-facing surface 15 of the first waist region 18 toward the wearer-facing surface 15 of the second waist region 20.

In some embodiments, although not illustrated, the diaper pant 10 may comprise an elasticized waistband. In some embodiments, the elasticized waistband may provide improved fit and containment and may be configured to elastically expand and contract laterally to dynamically fit a wearer's waist. The elasticized waistband may extend longitudinally inwardly from a waist edge of the diaper pant 10. In some embodiments, the diaper pant 10 may have two elasticized waistbands, one positioned in the second waist region 20 and one positioned in the first waist region 18, although other pant embodiments may be constructed with a single elasticized waistband. The elasticized waistband may be constructed in a number of different configurations including those described in U.S. Pat. Nos. 4,515,595 and 5,151,092, both of which are incorporated by reference herein in their entireties.

In some embodiments, the elasticized waistbands may comprise materials that have been "prestrained" or "mechanically prestrained" (i.e., subjected to some degree of localized pattern mechanical stretching to permanently elongate the material). The materials may be prestrained using suitable deep embossing techniques. In other embodiments, the materials may be prestrained by directing the material through an incremental mechanical stretching system as described in U.S. Pat. No. 5,330,458. The materials may then be allowed to return to their substantially untensioned condition, thus forming a zero strain stretch material that is extensible, at least up to the point of initial stretching. Examples of zero strain materials are disclosed in U.S. Pat. Nos. 2,075,189, 3,025,199, 4,107,364, 4,209,563, 4,834,741, and 5,151,092.

In some embodiments, referring to FIGS. 1 and 2 for example, the pant 10 may comprise the first and second side panels 28 and 30 attached at or adjacent the side edges 34 of the chassis 12 in one of the first waist region 18 or the second waist region 20. In various embodiments, each side panel 28 and 30 may either be a discrete separate component affixed to the chassis 12 or may comprise a unitary piece of material that is neither divided nor discontinuous with an element of the chassis 12, for example, a backsheet, a topsheet, or a leg cuff. In other various embodiments, a pair of laterally opposed side panels 28 and 30 may be attached adjacent the laterally opposing side edges 34 of the chassis 12 in the first waist region 18. In some embodiments, the first and second side panels 28 and 30 may be formed of a single component that may be attached to the backsheet 16 of the first waist region 18. In other various embodiments, the single component forming the first and second side panels 28 and 30 may be attached to the topsheet 14 of the first waist region 18, for example.

In some embodiments, the chassis 12 may comprise first and second laterally extending and longitudinally opposing end edges 36 and 38. The first end edge 36 may be positioned in the first waist region 18 and the second end edge 38 may be positioned in the second waist region 20. When the chassis 12 is folded about its lateral axis 26, the first end edge 36 may be positioned in a face-to-face orientation, or in a substantially face-to-face orientation, with the second end edge 38.

A simplified version of the assembly of the diaper pant 10 is illustrated in FIGS. 1-3. In FIG. 1, the chassis 12 is in an unfolded configuration and the first and second side panels 28 and 30 are in an unfolded configuration. The first and second side panels 28 and 30 may each be defined by the fold line 32 into first end regions 33 and second end regions 35. The first end regions 33 of the first and second side panels 28 and 30 may be connected to the first waist region 18. In some embodiments, the first and second side panels 28 and 30 may be connected to the garment-facing surface 17 of the first waist region 18, although it is to be appreciated that such side panels may also be connected to the wearer-facing surface 15 of the first waist region 18, for example. In FIG. 2, the chassis 12 has been folded (i.e., bi-folded) about the lateral axis 26, such that the first waist region 18 is in a face-to-face orientation with the second waist region 20 and the first and second side panels 28 and 30 remain in the unfolded configuration. In FIG. 3, the second end regions 35 of the first and second side panels 28 and 30 are folded laterally inward toward the longitudinal axis 24 about the fold line 32 and are connected to the second waist region 20 using a bond 21, such as a permanent bond, for example, or other suitable method of attachment. Some suitable methods of attachment of the second end regions 35 to the second waist region 20 comprise heat bonding, pressure bonding, and the use of adhesives or cohesives, for example. In various embodiments, the second end regions 35 may be removably or refastenably connected to the second waist region 20 using hook and loop fasteners, for example. In some embodiments, the second end regions 35 may be connected to the garment-facing surface 17 of the second waist region 20 to form a waist opening and two leg openings in the diaper pant 10. If the chassis 12 was folded about its lateral axis 26 after the second end regions 35 were folded about the fold line 32, then the second end regions 35 may be connected to the wearer-facing surface 15 of the second waist region 20.

In some embodiments, referring to FIGS. 1-5, the first and second side panels 28 and 30 may each comprise an end edge 40 and the chassis 12 may comprise the first end edge 36 in the first waist region 18. When the first and second side panels 28 and 30 are connected to the first waist region 18, the first end edge 36 may extend more distally with respect to the lateral axis 26 than the end edges 40 thereby forming a top hat 41 (see e.g., FIG. 5). In some instances, the top hat 41 may be undesirable from an aesthetic standpoint. In FIGS. 1-3 and 5, the first and second side panels 28 and 30 are formed from a single component that comprises the end edge 40, while in FIG. 4 the first and second side panels 28 and 30 are formed from separate components each comprising an end edge 40. In some embodiments, referring to FIG. 6, the single component forming the first and second side panels 28 and 30 may comprise an end edge 40 and the chassis 12 may comprise the first end edge 36 in the first waist region 18. When the first and second side panels 28 and 30 are connected to the first waist region 18, the end edge 40 may extend more distally with respect to the lateral axis 26 than the first end edge 36. In such an embodiment, the single component forming the first and second side panels 28 and 30 may be cut and positioned suitably to land on or engage the first waist region 18 of the chassis 12 in the position illustrated in FIG. 6. Such positioning on the chassis 12 of the single component forming the first and second side panels 28 and 30 is discussed in greater detail below with respect to FIG. 10.

In some embodiments, referring to FIGS. 7 and 8, the single component forming the first and second side panels 28 and 30 may comprise an end edge 40 and the chassis 12 may comprise the first end edge 36 in the first waist region 18. When the first and second side panels 28 and 30 are attached to the first waist region 18, the end edge 40 may extend to the same extent as the first end edge 36 with respect to the lateral axis 26. Referring to FIG. 8, such a diaper pant 10 may be formed by cutting or trimming, in the cross-direction, along cut line 42. A second cut may be made along cut line 44 and then the excess material 46 may be removed. Such cutting steps may reduce the chance that the first end edge 36 of the first waist region 18 extends beyond the end edge 40 of the single component forming the first and second side panels 28 and 30 for aesthetic reasons, for example. In such a fashion, the top hat 41 (FIG. 5) may also be eliminated.

In some embodiments, referring to FIG. 9, a continuous assemblage 13 of unfolded diaper pants 10 (similar to the pant 10 illustrated in FIG. 1, for example) with the first and second side panels 28 and 30 connected to the first waist region 18 may be advanced in a machine direction on a conveyor 48. The conveyor 48 may comprise an endless belt. In some embodiments, the wearer-facing surface 15 may be in contact with the conveyor 48. The conveyor 48 may comprise vacuum zones configured to place a vacuum force on at least a portion of the diaper pant 10 to hold the diaper pant 10 thereto. In other various embodiments, other retaining members or processes may be used to hold the diaper pant 10 to the conveyor 48. The retaining of the diaper pant 10 may be released at an appropriate time, such as when the diaper pant 10 is transferred from one conveyor to another. As discussed above, the first and the second side panels 28 and 30 may be formed of a single component or may each be formed of separate components. In any event, the first end regions 33 of the first and second side panels 28 and 30 may be connected to the first waist region 18 on either the wearer-facing surface 15 or the garment-facing surface 17 of the chassis 12.

In the illustrated embodiment, the diaper pant 10 is part of the continuous assemblage 13 that is separated into discrete diaper pants 10 using a cutting drum 62 and an anvil drum 64. The cutting drum 62 and anvil drum 64 may be positioned such that they can cut the continuous assemblage 13 in the machine direction to create a series of discrete diaper pants 10. The cutting drum 62 and the anvil drum 64 may use a cut and slip technique to space sequential diaper pants 10 about the rotating drum 58. A cut and slip technique is an operation for achieving spacing between discrete components. An example operation for achieving spacing between discrete components is disclosed in U.S. Pat. No. 5,702,551, which is incorporated by reference herein in its entirety. Other types of operations and equipment that may be used to cut and space discrete lengths of components are disclosed in U.S. Pat. Nos. 6,620,276; 6,811,019; and 7,587,966, which are incorporated by reference herein in their entireties. In some embodiments, the diaper pant 10 is cut into discrete articles upstream of the conveyer 48. In other embodiments, the cutting drum 62 and the anvil drum 64 may cut the continuous stream of articles into individual diaper pants 10 without introducing any significant space in between sequential diaper pants. In any event, after the cutting process, the unfolded diaper pant 10 may be transferred to a rotating drum 58, which is capable of high-speed folding of diaper pants. The rotating drum 58 may comprise vacuum ports, for example, to apply a vacuum or suction force to the diaper pant 10 to maintain its relative position on the rotating drum 58. In some embodiments, at least one portion of the garment-facing surface 17 of the chassis 12 is in direct contact with the rotating drum 58.

Generally, the rotating drum 58 may provide multiple folds to the diaper pant 10 in similar or different axes. For example, as described in more detail below, the rotating drum 58 may bi-fold the chassis 12 along the lateral axis 26 and fold the first and second side panels 28 and 30 about the fold lines 32 (FIG. 1). The rotating drum 58 may bi-fold the chassis 12 before or after the first and second side panels 28 and 30 are folded. If it is desired to attach the first and second side panels 28 and 30 to the garment-facing surface 17 of the chassis 12, the chassis 12 is first bi-folded on the rotating drum 58 and then the first and second side panels 28 and 30 are folded along the fold lines 32 (either sequentially or generally simultaneously). Comparatively, if it is desired to attach the first and second side panels 28 and 30 to the wearing-facing surface 15 of the chassis 12, the first and second side panels 28 and 30 are first folded along the fold lines 32 on the rotating drum 58 (either sequentially or generally simultaneously) and then the chassis 12 is bi-folded on the rotating drum 58.

Furthermore, in some embodiments, the bi-folding process and the panel-folding process may at least partially overlap. For example, if the chassis 12 is bi-folded before the first and second side panels 28 and 30 are folded, the bi-folding process does not have to completely finish before the panel-folding process begins. Similarly, if the first and second side panels 28 and 30 are folded before the chassis 12 is bi-folded, the panel-folding process does not have to completely finish before the bi-folding process begins. By allowing at least some of the folding processes to overlap, the amount of time needed for one diaper pant 10 to be sequentially folded along multiple fold lines may be decreased.

Still referring to FIG. 9, during rotation of the rotating drum 58, the diaper pant 10 may pass through a variety of stages or sectors. In the illustrated embodiment, the diaper pant 10 passes through five stages. During some of the stages, various folding members housed by the rotating drum 58 sequentially or simultaneously actuate to perform the required folds. In some embodiments, the stages may at least partially overlap. Stage A is the portion of the rotation where the diaper pant 10 is transferred onto the rotating drum 58. Stage B is the portion of the rotation where the chassis 12 is bi-folded (e.g., folded into the configuration illustrated in FIG. 2) while the diaper pant 10 remains positioned on the rotating drum 58. Stage C is the portion of the rotation where the first and second side panels 28 and 30 are folded along the fold lines 32 (e.g., folding into the configuration illustrated in FIG. 3) without transferring the diaper pant 10 to a separate folding drum. In some embodiments, stage C may occur after stage B. In other words, the first and second side panels 28 and 30 may be folded along the fold lines 32 prior to the bi-folding of the chassis 12. Stage D is the portion of the rotation where the first and second panels 28 and 30 may be bonded or otherwise attached to the garment facing surface 17. As is to be appreciated, if stage C occurs after stage B, the first and second panels 28 and 30 may be bonded or otherwise attached to the wearer facing surface 15 during stage D. Nevertheless, stage D is optional, as in some embodiments, the first and second panels 28 and 30 may be bonded or otherwise attached to the garment facing surface 17 after the diaper pant 10 has been discharged from the rotating drum 58. Stage E is the portion of the rotation where the diaper pant 10 is discharged from the rotating drum 58. The diaper pant 10 may be discharged, for example, onto a second conveyer 60 or other conveying device, such as a drum. In some embodiments, more or less stages or sectors may be utilized. Each stage is described in more detail below.

Figure 11:
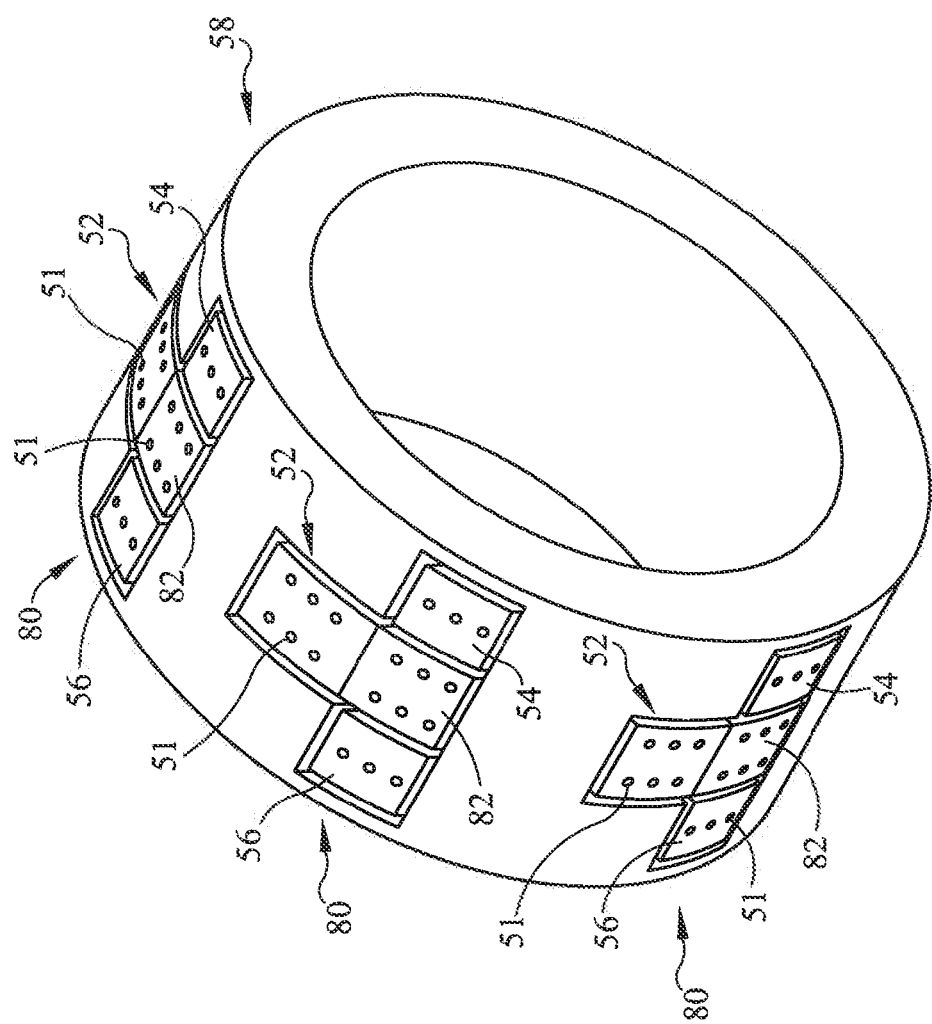
FIG. 11 is a perspective view of a rotating drum in accordance with one non-limiting embodiment of the present disclosure.

Referring now to stage A in FIG. 9, when the unfolded diaper pant 10 is transferred onto the rotating drum 58, it is placed proximate to a chassis folding member 52, a first panel folding member 54, and a second panel folding member 56 (FIG. 11). The diaper pant 10 is rotated into stage B where the chassis folding member 52 may pivot from a surface 59 of the rotating drum 58. The pivot axis may be generally coincident with the lateral axis 26 of the chassis 12. As discussed in more detail below, the pivot axis may be a "virtual axis." Through contact with the second waist region 20, the chassis folding member 52 may pivot the second waist region 20 towards to the first waist region 18 in the direction indicated by arrow 53. In some embodiments, the second waist region 20 is pivoted about 180 degrees during the folding motion. The chassis folding member 52 may be configured to hold or otherwise stabilize the second waist region 20 during the folding motion. In some embodiments, for example, the chassis folding member 52 may have vacuum ports to which a vacuum is applied. In this manner, the second waist region 20 is held in position on the chassis folding member 52 by vacuum, or suction, forces, during the folding movement. Once the fold has been made, the vacuum force may be removed from the chassis folding member 52 to release the hold on the second waist region 20. Vacuum can be applied in various ways, such as suitable arrangements of pumps, tubes, and vacuum ports. In some embodiments, at the completion of the folding movement, compressed air may be expelled from the vacuum ports to instigate a rapid release of the second waist region 20 from the chassis folding member 52. Other means for stabilizing web materials can be used as well. For example, the chassis folding member 52 can have a light-tack adhesive such that the second waist region 20 is removably adhered in place during the folding process.

The chassis folding member 52 may also have any suitable configuration. For example, the chassis folding member 52 may be a plate, a frame, one or more arms, or a variety of other configurations. The folding member 52 may also include any suitable drive means, such as mechanical linkages or hydraulic members, for example. After the chassis folding member 52 has pivoted the second waist region 20 and positioned it into a facing relationship with the first waist region 18, the chassis folding member 52 may pivot away from the bi-folded chassis 12. Subsequent to the bi-fold, the first end edge 36 may be aligned with, or substantially aligned with, the second end edge 38. In such a configuration, the wearer-facing surface 15 of the first waist region 18 may be in a face-to-face relationship with the wearer-facing surface 15 of the second waist region 20.

The rotating drum 58 may configured to fold the first and second side panels 28 and 30 at or about at the fold line 32 to land the second end regions 35 of the first and second side panels 28 and 30 on the garment-facing surface 17 of the second waist region 20 during stage C of the rotation. The folding of the first and second side panels may be made sequentially or generally simultaneously. The diaper pant 10, when entering stage C, will have its second end regions 35 of the first and second side panels 28 and 30 in an unfolded configuration, similar to the side panel configuration illustrated in FIGS. 1 and 2. In such a configuration, the plane of the second end regions 35 of the first and second side panels 28 and 30 may be parallel with, or substantially parallel with, the plane of the garment-facing surface 17 of the second waist region 20. During stage C, the second end regions 35 of the first and second side panels 28 and 30 will first be pivoted about 90 degrees with respect to the plane of the garment-facing surface 17 of the second waist region 20. The first and second side panels 28 and 30 may be pivoted by the first panel folding member 54 and the second panel folding member 56 (FIG. 11). In such a configuration, the plane of the wearer-facing surface 15 of the second end regions 35 of the first and second side panels 28 and 30 may be perpendicular to, or substantially perpendicular to, the plane of the garment-facing surface 17 of the second waist region 20. As the folding motion progresses, the first and second side panels 28 and 30 will eventually pivot about 180 degrees with respect to the plane of the garment-facing surface 17 of the second waist region 20. In such a configuration, the wearer-facing surface 15 of the second end regions 35 of the first and second side panels 28 and 30 will be in a face-to-face relation with the garment-facing surface 17 of the second waist region 20 (e.g., as shown in FIG. 3). The second end regions 35 of the first and second side panels 28 and 30 may then be connected to, attached to, bonded to, adhered to, and/or otherwise engaged with the garment-facing surface 17 of the second waist region 20 during stage D. Suitable connection, attachment, bonding, and/or adhering techniques may include heating, melting, bonding, gluing, ultrasonic bonding, and hot air bonding, for example. In some embodiments, the second end regions 35 of the first and second side panels 28 and 30 may be attached using removable or refastenable techniques, such as hook and loop fasteners, for example. The pant diaper pant 10 may then be transferred onto the second conveyor 60 during stage E upon release of vacuum or retaining force on the diaper pant 10 by the rotating drum 58. In some embodiments, the connection between the second end regions 35 of the first and second side panels to the second waist region 20 may take place on the second conveyor 60 or elsewhere downstream of the rotating drum 58.

Figure 10:
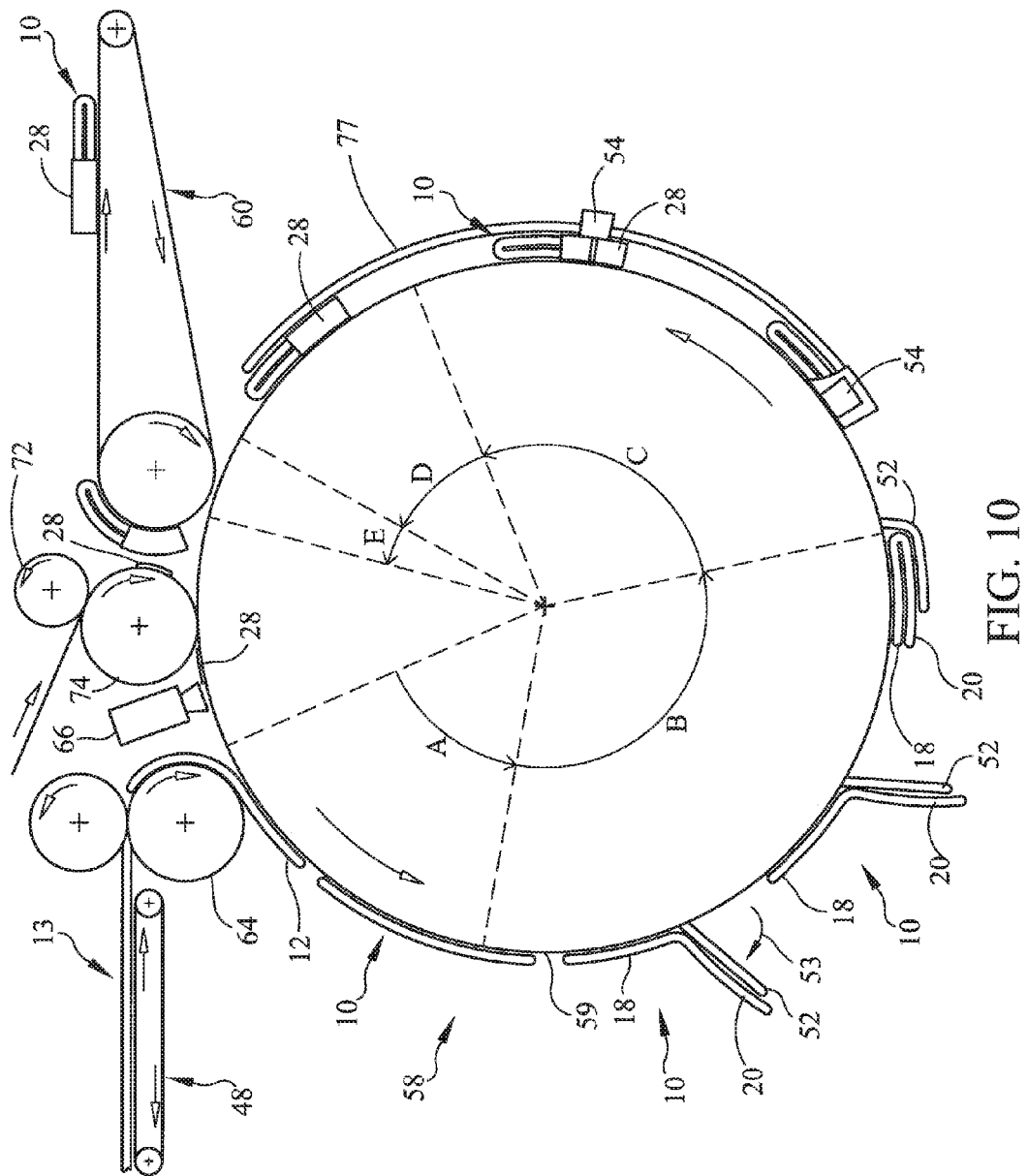
FIG. 10 is another schematic illustration of a diaper pant being assembled in accordance with one non-limiting embodiment of the present disclosure.

Referring now to FIG. 10, in some embodiments the chassis 12 may not be connected to the first and second side panels (either as a single component or as multiple components) until after it has been transferred to the rotating drum 58. In such an embodiment, a cutting drum or knife 72 and an anvil drum 74 may be positioned such that they can cut and apply the first and second side panels 28 and 30 to the rotating drum 58. The knife 72 and the anvil drum 74 may apply the first and second side panels 28 and 30 to the rotating drum using a cut and slip technique to properly space the first and second side panels 28 and 30 to line up with the chassis 12. The continuous assemblage 13 may be fed into the nip of the cutting drum 62 and the anvil drum 64 may also use a cut and slip technique to space each sequential chassis 12 about the rotating drum 58 to introduce a separation between sequential chassis. During the manufacture of a diaper pant similar to the diaper pant illustrated in FIG. 6, for example, when the chassis 12 is transferred to the rotating drum 58 it must be at least slightly spaced from the chassis immediately trailing the chassis 12. By introducing the space between sequential chassis, the single component forming the first and second side panels 28 and 30 may be attached to each chassis 12 without overlapping the trailing chassis. In the illustrated embodiment, an adhesive supplying apparatus 66, such as a spray nozzle, for example, may be positioned proximate to the rotating drum 58. The adhesive supplying apparatus 66 may supply an adhesive, such as glue, for example, to a portion of the first and second side panels 28 and 30 after they have been applied to the rotating drum 58. In such an embodiment, when the chassis 12 is transferred onto the rotating drum 58, the first and second side panels 28 and 30 may be connected to the first waist region 18 to form the diaper pant 10. The placement of the first and second side panels 18 and 20 will be suitably timed with the frequency of the chassis 12 being positioned on the rotating drum 58 using the cut and slip technique such that the first and second side panels 28 and 30 may be suitably positioned to be connected to the first waist region 18. The rotating drum 58 may then proceed to bi-fold the chassis 12 and fold the first and second side panels as described above with respect to FIG. 9.

It is to be appreciated that in some embodiments, hot air may be used to connect the first and second side panels 28, 30 with the first waist region 18 instead of or in addition to using adhesive supply apparatus 66 to supply adhesive. In such a configuration, the rotating drum 58 may be configured to direct hot air from inside the rotating drum 58 to overlapped portions of the side panels 28, 30 and the first waist region 18 of the chassis 12 to melt bond the side panels 28, 30 with the chassis 12.

In some embodiments, referring to FIG. 10, a guide 77 may be positioned at least partially around the rotating drum 58 and spaced from the outer surface 78 of the rotating drum 58. The guide 77 may be used to maintain the chassis 12 in the bi-folded configuration. In on embodiment, the guide 77 may be comprised of a material having a low coefficient of friction such that the guide 77 may slidably engage the garment-facing surface 17 of the second waist region 20 to maintain the wearer-facing surface 15 of the second waist region 20 in a face-to-face orientation with the wearer-facing surface 15 of the first waist region 18 as the rotating drum 58 rotates. In some embodiments, the guide 77 may comprise a conveyer or other elements suitable to maintain the diaper pant 10 in the folded the position. The guide 77 may have a lateral width smaller than the lateral width of the chassis 12, such that the first and second side panels 28 and 30 may be folded without contacting the guide 77.

FIG. 11 is a perspective view of the rotating drum 58 in accordance with one non-limiting embodiment. Various components have been removed, exaggerated, or otherwise simplified, for clarity. The rotating drum 58 comprises a plurality of stations 80, each of which are configured to receive a diaper pant 10 and perform multiple folds. The rotating drum 58 may have any suitable number of stations 80. As illustrated, each station 80 comprises a chassis folding member 52. The chassis folding member 52 is illustrated as a pivoting plate having a plurality of vacuum ports 51 to deliver a retaining force to the second waist region 20 before and during the folding motion. Each station 80 also comprises a first waist region zone 82 which receives and retains the first waist region 18 during the rotation of the rotating drum 58. The first waist region zone 82 also may utilize vacuum ports to aid in the retention of the diaper pant 10. As is to be appreciated, the vacuum ports positioned in the first wait region zone 82 may be operated separately from the vacuum ports poisoned on the chassis folding member 52. Each station 80 also comprises a first panel folding member 54 and the second panel folding member 56. The first and second panel folding members 54 and 56 may comprises a plurality of vacuum ports 51 to deliver a retaining force to the first and second side panels 28 and 30 before and during the folding motion. As described in more detail below with respect to FIG. 12, the first and second panel folding members 54 and 56 may be configured to move, pivot, and/or rotate toward each other and radially outward relative to the outer surface 59 to effect the side panel folds.

Generally, the rotating drum 58 allows a diaper pant 10 to be folded along multiple fold lines without needing to transfer the diaper pant 10 between multiple manufacturing components. Instead, the first and second side panels 28 and 30 may be held in place (e.g., "static") while the chassis is bi-folded. The first and second side panels 28 and 30 may then immediately be folded without an intermediate transfer step or other type of manipulation of the article. The elimination of transfer steps and overall reduction in the amount of article handling increases fold precision and reduces manufacturing time.

Figure 12:
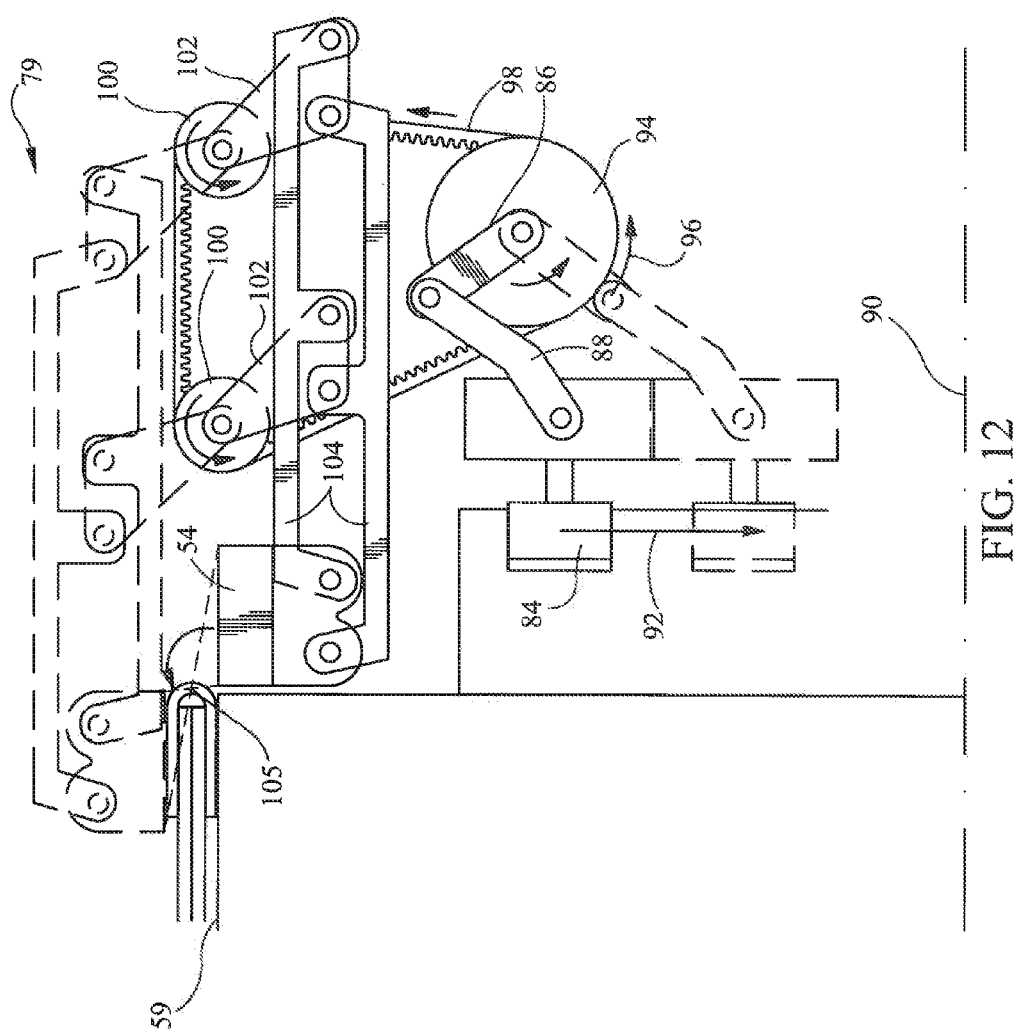
FIG. 12 is a schematic illustration of a folding mechanism in accordance with one non-limiting embodiment of the present disclosure.

Referring now to FIG. 12, the first panel folding member 54 will now be described in greater detail in accordance with one non-limiting embodiment. As is to be appreciated, the second panel folding member 56 (FIG. 11) may be configured similarly to the first panel folding member 54. The first panel folding member 54 is operatively engaged with a folding mechanism 79. The first panel folding member 54 may be configured to move, pivot, and/or rotate radially outward relative to the outer surface 59. In various embodiments, multiple pairs of first and second panel folding members 54 and 56 may be provided on the rotating drum 58. A pair of first and second panel folding members 54 and 56 is generally provided for each pant diaper receiving area on the rotating drum 58. For example, if the rotating drum 58 could hold four diaper pants 10 at once, four pairs of first and second panel folding members 54 and 56 may be provided on the rotating drum 58, such that the first and second side panels 28 and 30 for each diaper pant 10 may be folded as the drum 58 continually rotates.

In various embodiments, the first and second panel folding members 54 and 56 are not attached to the outer surface 59 of the rotating drum 58 and are movable, rotatable, and/or pivotable relative to the outer surface 59 through the use of the folding mechanisms 79 which each comprise linkages that may be operatively linked to a cam follower 84. The cam follower 84 may be captured inside a cam track (not shown) and move in accordance with the profile of the cam track during rotation of the rotating drum. In some embodiments, a primary linkage 86 may be operatively attached by a suitable pivot arm 88 to the cam follower 84, relative to an axis 90. Upon rotation of the rotating drum 58 around the axis 90, the cam follower 84 may move in a direction as indicated by arrow 92. The radial motion of cam follower 84 inwardly with respect to axis 90, may initiate the folding motion of the first and second panel folding members 54 and 56 (only the first panel folding member 54 is illustrated in FIG. 12 for clarity in illustration). More specifically, as the cam follower 84 moves, the primary linkage 86 may rotate a belt drive 94 to rotate in the direction indicated by arrow 96. The belt drive 94 may move a belt 98, which thereby turns at least one drive roller 100, which turns an associated linkage connector 102, which itself is operatively connected to a linkage 104 which comprises a cooperating pair of links that are configured to facilitate an about 180 degree fold-over motion of the first panel folding member 54. Other supporting links, shafts, bearings, and the like, which are not necessarily shown, may be configured in known ways to complete the first and second panel folding members 54 and 56. It may be desirable to design the belt drive 94 to have a diameter exactly twice the diameter of drive roller 100, such that as belt drive 94 rotates through an arc of 90 degrees, the drive roller 100 rotates through 180 degrees.

The first panel folding member 54 may move about a virtual axis 105 during the panel folding process. The virtual axis 105 may be generally aligned with the fold line 32 (FIG. 1). As illustrated, no equipment associated with the folding mechanism 79 is physically occupying the space of the virtual axis 105. The folding mechanism associated with bi-folding the chassis 12 may also utilize a virtual axis similar to the virtual axis 105 illustrated in FIG. 12. Using a virtual axis for the bi-folding of the chassis 12 is particularly beneficial due to the relatively thick gauge of a bi-folded chassis.

In some embodiments, still referring to FIG. 12, the first panel folding member 54 may also be configured to retain, hold, and/or otherwise stabilize the first side panel 28 during the folding motion. Likewise, the second panel folding member 56 may also be configured to retain, hold, and/or otherwise stabilize the second side panel 30 during the folding motion (although the second panel folding member 56 is not illustrated in FIG. 12 for clarity in illustration). In various embodiments, the first panel folding member 54 may have vacuum ports 51 (FIG. 11) to which a negative pressure or vacuum is applied. In this manner, the first side panel 28 may be held in position on the first panel folding member 54 by vacuum or suction forces. Once the second end region 35 of the first side panel 28 has been folded about the fold line 32 or otherwise, the vacuum, suction, and/or other retaining force may be removed from the first panel folding member 54 to release the hold on the second end region 35 of the first side panel 28. Other methods of retaining or stabilizing web, elastic, and/or side panel materials may also be used. For example, the first panel folding member 54 may have a light-tack adhesive applied to a surface thereof, such that the second end region 35 of the first side panel 28 may be removably adhered in place during the folding process. Additional details regarding rotating drum 58 and the first and second panel folding members 54 and 56 may be found in U.S. Pat. No. 7,368,027 and U.S. Patent Publication No. 2003/0088227, both of which are incorporated by reference herein in their entireties.

FIG. 13A is a linear view of the surface 59 of the rotating drum 58. FIG. 13B is an elevational side linear view of the rotating drum 58 corresponding to FIG. 13A. While the outer surface 59 of the rotating drum 58 is curved, FIGS. 13A and 13B illustrate a linear view of the rotating drum 58 for clarity. The stages A, B, and C that are illustrated in FIGS. 13A and 13B generally correspond with the stages illustrated in FIGS. 9 and 10. During stage A, the diaper pant 10 may be situated on the rotating drum 58, such that the first waist region 18 and a portion of the crotch region 22 are in direct contact with the outer surface 59 of the rotating drum 58, and such that the first and second side panels 28 and 30 extend laterally outward from the first waist region 18 with the first side panel 28. The first and second side panels 28 and 30 may be positioned on at least a portion of the first panel folding member 54 and the second side panel 30 positioned on at least a portion of the second panel folding member 56. In some embodiments, the second end regions 35, or portions thereof, of the first and second side panels 28 and 30 may be positioned on the first and second panel folding members 54 and 56, respectively. The second waist region 18 and a portion of the crotch region 22 may be positioned on at least a portion of the chassis folding member 52.

In the illustrated embodiment the diaper pant 10 is delivered to the rotating drum 58 in their longitudinal direction (e.g., parallel to longitudinal axis 24), and in particular with the second laterally extending edge 38 first. It is understood, however, that the diaper pants 10 may be delivered longitudinally to the rotating drum 58 with the first laterally extending edge 36 first, or they may be delivered transversely (e.g., side edge 34 first) to the rotating drum 58.

During stage B, the chassis folding member 52 pivots outward from the surface 59 of the rotating drum 58 in the direction indicated by arrow 53 to bi-fold the chassis 12. As illustrated, the chassis folding member 52 may comprise a first folding arm 52*a* and a second folding arm 52*b*. The bi-folded chassis 12 may be maintained in the folded position by the guide 77. In the illustrated embodiment, the guide 77 comprises a conveyor 110. The conveyer 110 may be a single conveyor (as illustrated), a conveyer assembly, or other biasing element or collection of elements. The offset distance "d" of the conveyer 110 from the surface 59 of the rotating drum 58 may be similar to the thickness of a bi-folded chassis 12. The chassis folding member 52 may pivot or otherwise move towards the surface 59 of the rotating drum 58 in the direction indicated by arrow 55. The conveyer 110 may be laterally positioned intermediate the first folding arm 52a and the second folding arm 52b such that the chassis folding member 52 can pivot back toward the rotating drum 58 without interfering with the conveyer 110 upon completion of the fold.

As the diaper pant 10 passes through stage C, the first and second panel folding member 54 and 56 actuate to fold the first and second side panels 28 and 30. As shown, the first and second panel folding members 54 and 56 may begin to actuate before the chassis folding member 52 has fully returned to the surface 59 of the rotating drum. As illustrated, the conveyer 110 has a lateral width smaller than the lateral spacing between the first and second panel folding members 54 and 56 in the fully actuated position such that they may be actuated without contacting the conveyer 110.

Figure 14:
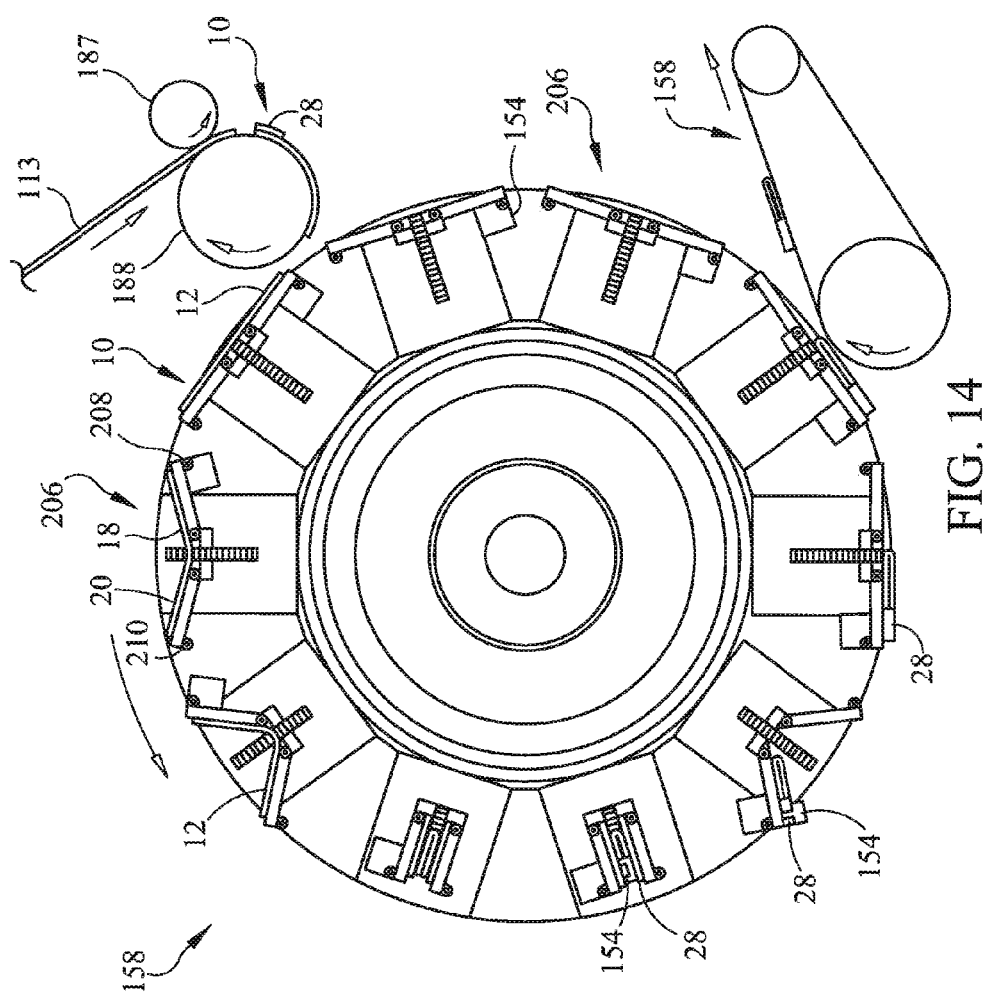
FIG. 14 is a schematic side elevation of a rotating drum in accordance with one non-limiting embodiment of the present disclosure.

In some embodiments, instead of folding one of the first or second waist regions by about 180 degrees to effect the fold, both the first and second waist regions may each be pivoted toward each other by about 90 degrees to bi-fold the chassis 12. Suitable bi-folding techniques for absorbent articles and diaper pants are disclosed in U.S. Pat. Nos. 5,779,831 and 7,322,925 and Japanese Patent Publication No. 07205943 A2, which are all incorporated by reference herein in their entireties. FIG. 14 is a schematic side elevation of one embodiment of rotating drum 158 for bi-folding the chassis 12 by pivoting each of the first and second side panels 28 and 30 by about 90 degrees.

The rotating drum 158 may be constructed of suitable frame structure 201 and operatively connected to a central shaft 204 that is in turn driven by a suitable drive motor (not shown) for rotation on the axis of the shaft to define a transport direction in which the rotating drum 158 moves as indicated by the direction arrow in FIG. 14. A plurality of folding devices, generally indicated at 206, are carried by the rotating drum 158 (e.g., ten such folding devices are illustrated on the rotating drum of FIG. 14). The number of folding devices 206 may vary depending at least in part on the size of the rotating drum, the size of the article to be folded, and the desired speed of the manufacturing line of which the rotating drum 158 is part. The folding device 206 is also operable to bi-fold the chassis 12 such that the first and second waist regions 28 and 30 of the diaper pant 10 are in opposed relationship with each other. Additionally, the folding devices 206 may be configured to fold portions of the first and second side panels 28 and 30 before or after the chassis 12 is bi-folded.

Each folding device 206 of the illustrated embodiment may comprise a pair of folding plates 208 and 210 that are moveable relative to the rotating drum 158 between an open configuration (e.g., as illustrated at angular positions A, G, H, I and J in FIG. 14) in which the plates lie generally in the same plane as each other and are oriented generally tangentially relative to the rotating drum and a closed configuration (e.g., as illustrated at angular positions D and E in FIG. 14) in which the plates are in opposed relationship with each other and oriented generally radially relative to the rotating drum. The term longitudinal as used herein in reference to the folding device 206, and more particularly to the folding plates 208 and 210, refers to the direction extending from one end of each folding plate to the opposite end of the same folding plate. For example, in the open configuration of the folding device 206 the longitudinal direction of each folding plate 208 and 210 is tangential to the rotating drum 158 and in the closed position of the folding device the longitudinal direction of each folding plate is generally parallel to the radius of the rotating drum. The terms transverse and lateral as used herein in reference to the folding device 206 refer to the direction orthogonal to both the longitudinal direction and the radius of the rotating drum 158, such as parallel to the rotation axis of the rotating drum. The folding plates 208 and 210 are suitably disposed adjacent the circumference of the rotating drum 158 in the open configuration of the plates, and are drawn relatively inward of the rotating drum circumference in the closed configuration of the folding device 206.

A continuous assemblage 113 of diaper pants may be fed through a nip formed between a cutting roll 187 and an anvil roll 188 to cut the web into discrete, diaper pants 10. The first and second side panels 28 and 30 may have been previously attached to the continuous assemblage 113 upstream of the cutting roll 187 and the anvil roll 188. The rotating drum 158 may be continuously driven to rotate on the central shaft 204 so that the multiple folding devices 206 on the rotating drum sequentially pass by the vacuum anvil roll 188 to receive the diaper pants 10 onto the folding devices 206. At the angular position of the rotating drum identified as angular position A in FIG. 14, the longitudinal folding plates 208 and 210 of one longitudinal folding device 206 have just passed the vacuum anvil roll 188 with the folding device 206 in its open configuration, i.e., with the folding plates spread apart and in generally planar relationship with each other tangential to the rotating drum 158.

As the rotating drum 158 further carries the diaper pant 10 in the transport direction (e.g., the counter-clockwise direction in the illustrated embodiment) to the angular position indicated in FIG. 14 as position B, the folding device 206 is pulled radially inward relative to the rotating drum. This motion results in the initiation of folding of the longitudinal folding plates 208 and 210, and hence the diaper pant 10 retained thereon. In some embodiments, a transverse tucking blade (e.g., a rotating or reciprocating tucking blade) separate from the rotating drum 158 may contact and push against the crotch region 22 (FIG. 1) of the diaper pant 10 as folding of the chassis 12 is initiated.

At angular position C of the rotating drum 158, the folding plates 208 and 210 are folded further inward toward the closed configuration of the longitudinal folding device 206. Upon further rotation of the rotating drum 158 to angular position D, the back and front folding plates 208 and 210 are in opposed relationship with each other in the closed configuration of the folding device 206. Accordingly, the chassis 12 of diaper pant 10 is folded so that the first and second waist regions 18 and 20 are in opposed relationship with each Upon rotation of the rotating drum 158 to angular position E in the embodiment of FIG. 14, a first panel folding member 154 may begin to fold the first side panel 28 of the diaper pant 10. A second panel folding member (not illustrated) may also begin to fold the second side panel 30 (FIG. 1) of the diaper pant 10. The first and second side panel folding members may be implemented similarly to the panel folding member illustrated in FIG. 12, or by any other suitable panel folding technique. At angular position E, the second end regions 35 (FIG. 1) of the first and second side panels 28 and 30 will be pivoted about 90 degrees with respect to the plane of the garment-facing surface 17 of the second waist region 20. At angular position F, the first and second side panels 28 and 30 may be pivoted about 180 degrees with respect to the plane of the garment-facing surface 17 of the second waist region 20. Similar to previously discussed embodiments, the first and second side panels 28 and 30 may instead be folded before the bi-folding of the chassis 12.

In some embodiments, at angular position G, the second end regions 35 of the first and second side panels 28 and 30 may then be connected to, attached to, bonded to, adhered to, and/or otherwise engaged with the garment-facing surface 17 of the second waist region 20 using any suitable techniques, such as using hook and loop fasteners, melting, or gluing, for example. The rotating drum 158 rotates further to angular position H at which the folding plates 208 and 210, in the open configuration of the folding device 206, are in generally opposed relationship with a suitable transfer device, such as a conveyor 158 illustrated in FIG. 14. The conveyor 158 draws the diaper pants 10 off of the rotating drum 158 and transfers the diaper pants 10 downstream of the folding device for further processing.

It is to be appreciated that the methods of assembly of diaper pants specifically described herein and illustrated in the accompanying drawings are non-limiting example embodiments. The features illustrated or described in connection with one non-limiting embodiment may be combined with the features of other non-limiting embodiments. Such modifications and variations are intended to be included within the scope of the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings, the method comprising:

connecting first end regions of the first and second side panels with the first waist region of the chassis;

advancing the chassis in a machine direction on a rotating drum having an outer surface, a chassis folding member, a first panel folding member, and a second panel folding member, wherein the backsheet in the second waist region is positioned on the chassis folding member, and wherein the first and second side panels extend laterally outward from the first waist region with the first panel positioned on the first panel folding member and the second side panel positioned on the second panel folding member;

pivoting the chassis folding member 180 degrees while applying vacuum forces to at least a portion of the backsheet to hold the chassis in contact with the chassis folding member, folding the chassis about the lateral axis by pivoting the second waist region 180 degrees to position the second waist region into a facing relationship with the first waist region;

moving the first panel folding member and the second panel folding member toward each other and radially outward relative the outer surface of the rotating drum to position second end regions of the first and second side panels in contact with the second waist region of the chassis; and connecting the second end regions of the first and second side panels with the second waist region.

2. The method of claim 1, wherein the backsheet in the first waist region is in direct contact with the outer surface of the drum, and wherein the chassis folding member pivots the second waist towards the first waist region.

3. The method of claim 1, further comprising the step of pivoting the first and second panel folding members away from each other after of the second end regions of the first and second side panels are connected with the second waist region.

4. The method of claim 1, wherein the second end regions of the first and second side panels are permanently connected with the second waist region.

5. The method of claim 1, wherein the second end regions of the first and second side panels are permanently connected with the second waist region using a heat seam.

6. The method of claim 1, wherein the second end regions of the first and second side panels are refastenably connected with the second waist region.

7. The method of claim 6, wherein the second end regions of the first and second side panels are refastenably connected with the second waist region with a hook and loop fastener.

8. The method of claim 1, wherein the first end regions of the first and second side panels are permanently connected with the first waist region.

9. The method of claim 1, wherein the first end regions of the first and second side panels are refastenably connected with the first waist region.

10. The method of claim 1, comprising applying vacuum forces to the first and second side panels to hold the first and second side panels in contact with the first and second folding members.

11. The method of claim 10, wherein the vacuum forces are applied only to the second end regions of the first and second side panels.

12. The method of claim 1, further comprising the step of transferring the folded chassis from the rotating drum to a conveying device.

13. The method of claim 12, wherein the crotch region of the folded chassis is transferred to the conveying device before the first waist region.

14. The method of claim 12, wherein the conveying device is one of a conveyor and a drum.

15. The method of claim 1, wherein moving the first panel folding member and the second panel folding member toward each other and radially outward relative the outer surface of the rotating drum to position second end regions of the first and second side panels in contact with the second waist region of the chassis comprises pivoting the first panel folding member and the second panel folding member.

16. The method of claim 15, wherein pivoting the first panel folding member and the second panel folding member comprises pivoting the first panel folding member about a virtual axis and pivoting the second panel folding member about a virtual axis.

17. A method for assembling disposable diaper pants, each diaper pant comprising a chassis, a first side panel, and a second side panel, each chassis comprising a topsheet, a backsheet, and an absorbent core disposed between the topsheet and the backsheet, each chassis having a first waist region longitudinally opposed to a second waist region, and a crotch region located between the first and second waist regions, and having a longitudinal axis and a lateral axis, the first and second side panels joining the first waist region and the second waist region to form a waist opening and a pair of leg openings, the method comprising:

connecting first end regions of the first and second side panels with the first waist region of the chassis;

advancing the chassis in a machine direction on a rotating drum having an outer surface, a chassis folding member, a first panel folding member, and a second panel folding member, wherein the backsheet in the second waist region is positioned on the chassis folding member, and wherein the first and second side panels extend laterally outward from the first waist region with the first panel positioned on the first panel folding member and the second side panel positioned on the second panel folding member;

pivoting each of the first panel folding member and the second panel folding member about a respective virtual axis toward each other and radially outward relative the outer surface of the rotating drum to position second end regions of the first and second side panels in contact with the second waist region of the chassis;

pivoting the chassis folding member 180 degrees while applying vacuum forces to at least a portion of the backsheet to hold the chassis in contact with the chassis folding member, folding the chassis about the lateral axis by pivoting the second waist region 180 degrees to position the second waist region into a facing relationship with the first waist region; and connecting the second end regions of the first and second side panels with the second waist region.

18. The method of claim 17, wherein the chassis is folded about a virtual axis.

* * * * *